United States Patent
Riehl et al.

(10) Patent No.: US 10,067,773 B2
(45) Date of Patent: Sep. 4, 2018

(54) COMPATIBILITY CHECKING FOR USER INTERFACE CUSTOMIZATION

(71) Applicant: SAP SE, Walldorf (DE)

(72) Inventors: Andreas Riehl, Wiesloch (DE); Sonja Barnet, Viernheim (DE); Gibo Thomas Pulipara, Heidelberg (DE)

(73) Assignee: SAP SE, Walldorf (DE)

( * ) Notice: Subject to any disclaimer, the term of this patent is extended or adjusted under 35 U.S.C. 154(b) by 267 days.

(21) Appl. No.: 15/248,177

(22) Filed: Aug. 26, 2016

(65) Prior Publication Data
US 2018/0059892 A1 Mar. 1, 2018

(51) Int. Cl.
*A61B 5/00* (2006.01)
*G06F 9/451* (2018.01)
*G06F 3/0484* (2013.01)
*G06F 3/0481* (2013.01)

(52) U.S. Cl.
CPC ............ *G06F 9/451* (2018.02); *A61B 5/7435* (2013.01); *G06F 3/0481* (2013.01); *G06F 3/0484* (2013.01)

(58) Field of Classification Search
CPC ...... G06F 3/0484; G06F 3/0481; A61B 5/743
See application file for complete search history.

(56) References Cited

U.S. PATENT DOCUMENTS

| | | | |
|---|---|---|---|
| 2014/0280368 A1* | 9/2014 | Kemmler | G06F 17/30294 707/803 |
| 2018/0059877 A1* | 3/2018 | Riehl | G06F 9/451 |
| 2018/0059878 A1* | 3/2018 | Riehl | G06F 17/30324 |

* cited by examiner

*Primary Examiner* — Shen Shiau
(74) *Attorney, Agent, or Firm* — Schwegman Lundberg & Woessner, P.A.

(57) ABSTRACT

Example embodiments of compatibility checking for user interface customization are described. In an example embodiment, a first user interface view including first data items is accessed, each of the first data items referencing a corresponding data item of a data source. Whether the first user interface view is referenced by a second user interface view is determined. Based on the first user interface view not being referenced by a second user interface view, changes to any of the first data items of the first user interface view are allowed during a design time of the first user interface view. Based on the first user interface view being referenced by the second user interface view, one or more of the first data items of the first user interface view being referenced by the second user interface view are identified, and changes to the identified data items are prevented.

20 Claims, 18 Drawing Sheets

GENERAL >>> FIELD SELECTION >>> FIELD PROPERTIES >>> PARAMETERS

DEPENDENCIES: 0
STATUS: INACTIVE

AVAILABLE FIELDS AND ASSOCIATIONS

| NAME | LABEL | FIELD TYPE | SELECT |
|---|---|---|---|
| SALESORDEROVERALLSTATUS | OVERALL STATUS | FIELD | ☐ |
| OPPORTUNITY | OPPORTUNITY ID | FIELD | ☐ |
| CUSTOMERCONTACTUUID | GENERIC NODE KEY | FIELD | ☐ |
| SHIPTOPARTYADDRESSUUID | GENERIC NODE KEY | FIELD | ☐ |
| BILLTOPARTYADDRESSUUID | GENERIC NODE KEY | FIELD | ☐ |
| SALESORDERPAYMENTMETHOD | PAYMENT METHOD | FIELD | ☐ |
| SALESORDERPAYMENTTERMS | PAYMENT TERMS | FIELD | ☑ |
| > TRANSACTIONCURRENCY | | ASSOCIATION | ☐ |
| CURRENCY | CURRENCY | KEY FIELD | ☑ |
| CURRENCYISOCODE | ISO CODE | FIELD | ☐ |
| > ITEM | | ASSOCIATION | ☐ |
| > CUSTOMERCONTACT | | ASSOCIATION | ☐ |
| > ADDRESS | CDS EDITOR TEST EPM ADDRESS | ASSOCIATION | ☑ |
| ADDRESSUUID | ADDRESS UUID | KEY FIELD | ☑ |
| CITYNAME | CITY | FIELD | ☐ |
| POSTALCODE | POSTALCODE | FIELD | ☐ |
| STREETNAME | STREET | FIELD | ☐ |
| HOUSENUMBER | BUILDING | FIELD | ☐ |
| COUNTRY | COUNTRY | FIELD | ☐ |
| ADDRESSTYPE | ADDRESS TYPE | FIELD | ☐ |

SELECTED FIELDS AND ASSOCIATIONS

| NAME | KEY | ALIAS | LABEL | ACTIONS |
|---|---|---|---|---|
| SALESORDERUUID | ☑ | SALESORDERUUID | SALES ORDER UUID | ⊠ |
| TRANSACTION_CURRENCY.CURRENCY | ☐ | CURRENCY | CURRENCY | ⊠ |
| SALESORDERPAYMENTTERMS | | SALESORDERPAYMENTTERMS | PAYMENT TERMS | ⊠ |
| ADDRESS.ADDRESSUUID | ☑ | ADDRESSUUID | ADDRESS UUID | ⊠ |

622 — FIELD SELECTION
624 — AVAILABLE FIELDS AND ASSOCIATIONS
626 — SELECTED FIELDS AND ASSOCIATIONS
630
600D

▼ object {4} ← 800
   ▶ root {8} ← 802
   ▼ fieldList [27] ← 804
      ▶ 0 {9}
      ▶ 1 {9}
      ⋮
      ▶ 25 {9}
      ▼ 26 {9} ← 806
         name : _CustomerContact ← 808
         label : (value)
         fieldType : A ← 810
         noChangeAllowed : false
         changeType : (value)
        ▶ annotation {4}
        ▶ dataTypeInfo {4}
        ▶ associationInfo {3}
        ▼ fieldList [18] ← 812
           ▶ 0 {9}
           ▶ 1 {9}
           ⋮
           ▶ 16 {9}
           ▼ 17 {9} ← 814
              name : _Address ← 815
              label : (value)
              fieldType : A ← 816
              noChangeAllowed : false
              changeType : (value)
             ▶ annotation {4}
             ▶ dataTypeInfo {4}
             ▶ associationInfo {3}
             ▶ fieldList [11] ← 818
   ▶ associationList [3] ← 820
   ▶ parameterList [0] ← 822

COMPATIBILITY CHECKING FOR USER INTERFACE CUSTOMIZATION

FIELD

The present application relates generally to data processing and, more specifically in an example embodiment, to compatibility checking for user interface customization.

BACKGROUND

To simplify the generation of a user interface, such as a graphical user interface (GUI), a currently used interface view may be employed as a base or starting point for generating a new, related user interface view. If a newer user interface view is generated in such a manner, changes to the older interface view that is employed as a base may adversely affect the newer interface view. For example, while additions to the older interface view are unlikely to affect the newer interface view, the deletion of one or more data items of the older interface view that are also displayed via the newer interface view will likely encounter an error during execution or, worse, return incorrect data for presentation to the user without any overt indication of an error.

BRIEF DESCRIPTION OF DRAWINGS

The present disclosure is illustrated by way of example and not limitation in the figures of the accompanying drawings, in which like references indicate similar elements.

FIG. 6B is a graphical representation of an example user interface for displaying selectable data items of a data source for inclusion in a user interface view.

FIGS. 6C and 6D are representations of an example user interface displaying data fields of a data source associated with a displayed data item of a data source.

FIG. 8 is a listing of an example data object including multiple associated levels of selectable data fields for inclusion in a user interface view.

FIG. 11 is a graphical representation of an example user interface for selecting data sources for a user interface view in which data dependency data and user interface view status are provided.

FIG. 12 is a graphical representation of an example user interface for displaying selectable data items of a data source for inclusion in a user interface view in which change compatibility guidance is provided.

DETAILED DESCRIPTION

In the following description, for purposes of explanation, numerous specific details are set forth to provide an understanding of various example embodiments of the present subject matter. It will be evident, however, to those skilled in the art, that example embodiments of the present subject matter may be practiced without these specific details.

Figure 1:
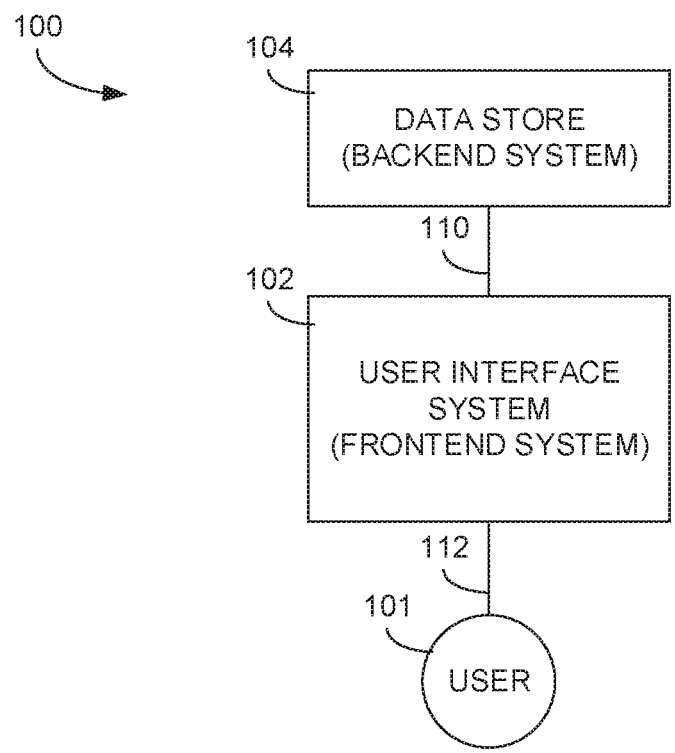
FIG. 1 is a block diagram of an example data processing system including an example user interface system.

FIG. 1 is a block diagram of an example data processing system 100 that may include a data store 104 serving at least as part of a backend computing system, and a user interface system 102 serving at least as part of a frontend system to communicate with one or more users 101 and the data store 104. The data store 104 may be coupled with the user interface system 102 by way of a first communication network or connection 110, while the user interface system 102 may be coupled with the user by way of a second communication network or connection 101. In an example embodiment, the user 101 may employ a client device, such as a desktop computer, laptop computer, tablet computer, smart phone, or the like to interact with the user interface system 102 operating on a server system via a communication network 112, such as a wide area network (WAN) (e.g., the Internet), a wireless WAN (WWAN), a local area network (LAN), a wireless LAN (WLAN), a cellular data network (e.g., a third-generation (3G) or fourth-generation (4G) network), another communication connection, and/or combinations thereof. In another example embodiment, the user interface system 102 may operate at least partially on the client device being employed by the user.

In turn, the user interface system 102 may communicate with the data store 104 via a similar communication network 110, or may operate on the same computing system as the data store 104. In a particular example, the user interface system 102 may communicate with the data store 104 by way of an access gateway system or other computing system facilitating access (e.g., read access, write/update access, and so on) to various data items stored in the data store 104.

One or more of the various components of the data processing system 100 depicted in FIG. 1 (e.g., the data store 104, the user interface system 102, or a client device employed by the user 101) may be, or may be hosted on, one or more computer or server systems, such as the computer processing system 1300 described below in conjunction with FIG. 13.

The data store 104 may be, in an example embodiment, a database system (e.g., a relational database management system (DBMS), an in-memory database system, or the like) storing and facilitating access to data associated with a commercial enterprise. For example, the data stored at the database system may include, but is not limited to, sales data, marketing data, engineering data, or human resources data. In other example embodiments, the data stored at the data store 104 is not limited to any particular type of data.

In an example embodiment, the user interface system 102 may facilitate the generation and customization of particular user interface "views" of the data stored in the data store 102, each of which displays or provides access to a different set of one or more data items stored at the data store 104. In an example embodiment, a view displays the results of one or more previously generated and stored database queries. Accordingly, a view may simplify access to data in one or more database tables by representing a subset of the data stored in a particular table, joining multiply database tables into a "virtual" table, and the like, thus hiding table complexity from the user. In another example embodiment, a view may employ one or more other views instead of a database table directly to retrieve data from the table. For example, a first user interface view may present to a user 101 multiple items of human resources data, such as a number of vacation days or hours currently available for a particular employee, a number of vacation days or hours accrued by the employee in a typical time period, and a number of vacation days or hours consumed by the employee during a current time period. In a second user interface view, data relating to a particular sale, such as a listing of items purchases, a quantity of each item, a sale price of each item, and the like, may be presented to the user 101. Many other types of customizable user interface views are possible in other example embodiments.

Figure 2:
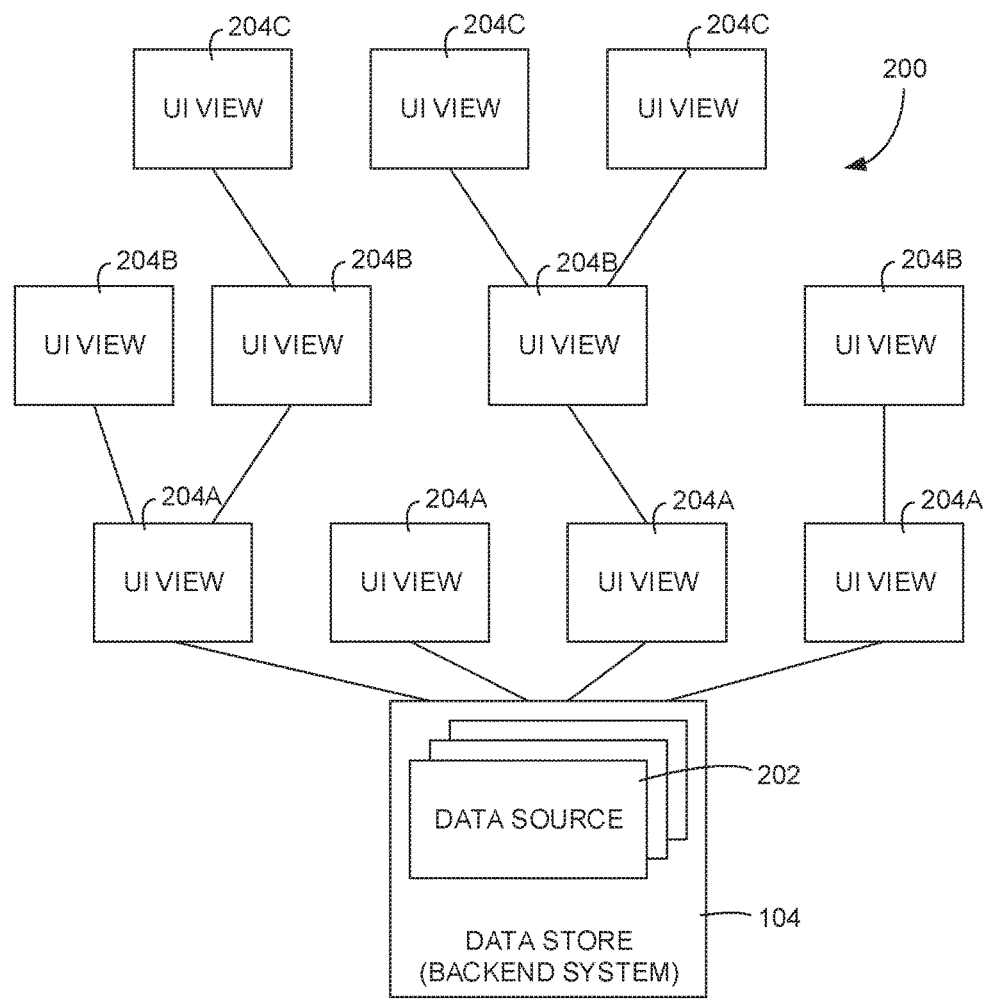
FIG. 2 is a block diagram of an example user interface view hierarchy.

FIG. 2 is a block diagram of an example user interface view hierarchy 200. More specifically, the data store 104 may facilitate access to one or more data sources 202, each of which includes one or more data items that may be accessed by the user 101 by way of one or more user interface views created by a user interface designer during a design time of the user interface views. In an example embodiment, the data store 104 may provide one or more designer utilities or services, which the designer may use to select one or more data items to be accessible via the user interface view. In some example embodiments, the designer services may provide some standardized user interface templates by which the selected data items may be presented to the user 101, such as an employee or manager of an organization. In an example embodiment, the data store 104 may provide sample or basic user interface view definitions upon which other user interface views may depend. Once designed, a typical user 101 may access one or more of the data items of the data sources 202 of the data store 104 via one or more of the user interface views 204 during a runtime of the user interface view being utilized.

As depicted in FIG. 2, a user interface view (e.g., user interface views 204A) may depend directly upon the services or user interface views provided by the data source 202. In addition, other user interface views (e.g., user interface views 204B) may each depend upon a previously generated user interface view 204A, while yet other user interface views (e.g., user interface views 204C) may each depend upon one of the second-level user interviews 204B. Additional levels of the overall user interface view hierarchy 200 may be presented in some example embodiments. In an example embodiment, a provider of the user interface system 102 may provide one or more levels of the user interface views 204 (e.g., the first-level user interface views 204A) upon which customers or third parties may build their own views without exposing the base data sources 202.

Figure 3A:
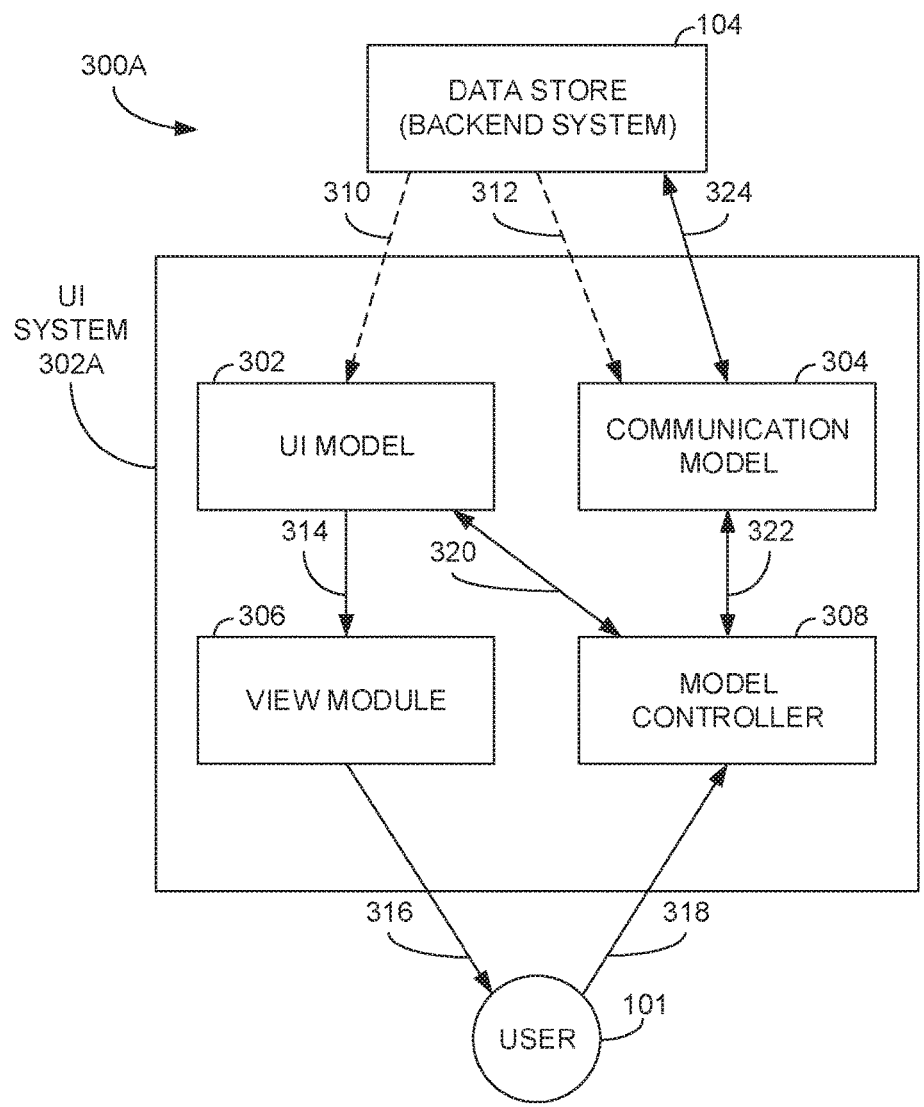
FIG. 3A is a block diagram of an example data processing system including an example user interface system employing two user interface models during a design time of a user interface view.

FIG. 3A is a block diagram of an example data processing system 300A including an example user interface system 302A including two user interface models 302 and 304 that may be employed during a design time of a user interface view. More specifically, in the particular example of FIG. 3A, the user interface system 302A may include a user interface model 302 and a communication model 304, along with a view module 306 and a model controller 308. Each component 302-308 of the user interface system 302A may be implemented in hardware, as software or firmware instructions executable on one or more hardware processors, or as some combination thereof.

In an example embodiment, the user interface model 302 may include first information identifying a plurality of data items stored at the data store 104. In some example embodiments, the plurality of data items may include fields of one or more database tables stored in the data store 104. Such fields may include data values and associations to other database tables. In other example embodiments, other types or forms of data items may be identified in the first information of the user interface model 302. Further, the first information may be held in one or more data structures 310 that are initially transferred from the data store 104 to the user interface model 302. In an example embodiment, the plurality of data items identified in the first information are available for user selection to be included in a user interface view. Also in an example embodiment, the first information may also include one or more indications of those of the data items that are currently being implemented in the user interface view being designed or updated.

The communication model 304 may include second information indicating which of the data items identified in the first information of the user interface model 302 have been selected for inclusion into the user interface view. In an example embodiment, the communication model 304 may initially receive the second information in one or more data structures 312 from the data store 104. For example, if a previously existing user interface view is to be modified, the data store 104 may provide information identifying the data items that are current accessible via that user interface view. During a design or update time of the user interface view, the communication model 304 may update the particular data items that have been selected for inclusion in the user interface view via interaction with the model controller 308, as is discussed in greater detail below.

The view module 306 may be configured to receive update information 314 from the user interface model 302 regarding changes or updates to the first information to be presented to the user 101. The view module 306 may also translate that information into viewable information 316 having a format utilized by the user interface system 302A, and may cause presentation of the viewable information 316 to the user 101 via the user interface system 302A.

The model controller 308 may be configured to receive user input 318 provided by the user 101 (e.g., via the user interface system 302A, such as by way of mouse click, text entry, or other input methods) and, based on that user input 318, update one or both of the user interface model 302 and the communication model 304. In an example embodiment, the user 101 may select one of the data items available from the data store 104, as provided by the user interface model 302 and presented by the view module 306, for inclusion in the user interface view currently being designed or updated. In response, the model controller 308 may provide an indication 322 of that selection to the communication model 304 to update the second information in the communication model 304 to include the newly selected data item. In addition, the model controller 308 may also provide an indication 320 of that same user selection to update the user interface model 302 to indicate that selection so that the user 101 may see a visual indication of that selection via the view module 306. Conversely, a user input 318 indicating a deselection of one of the data items may cause the model controller 308 to update the user interface model 302 and/or the communication model 304 accordingly via indications 320, 322.

In an example embodiment, the communication model 304 may update the data store 104 regarding the current state of the user interface view, such as by identifying the one or more data items that are currently being included in the user interface view. For example, the communication model 304 may keep the data store 104 updated on an ongoing basis by informing the data store 104 via an indication 324 each time a data item selection or deselection is received from the user 101. In another example embodiment, the communication model 304 may update the data store 104 by identifying the data items that are currently selected for access via the user interface view being created or updated in response to exiting or terminating the design time of the user interface view. In some instances, the indication 324 may be an updated version of the data structure 312 previously received from the data store 104.

In at least some example embodiments of the user interface system 302A of FIG. 3A, the use of two separate models (e.g., the user interface model 302 and the communication model 304) may facilitate the generation of customized user interface views. More specifically, one model (e.g., the user interface model 302) may provide a graphical user interface during a design time of a user interface view, thus providing the user 101 with the means to select available data items for the user interface view, while another model (e.g., the communication model 304) tracks the currently selected data items to be included in the user interface view and communicates that information to the data store 104.

Figure 3B:
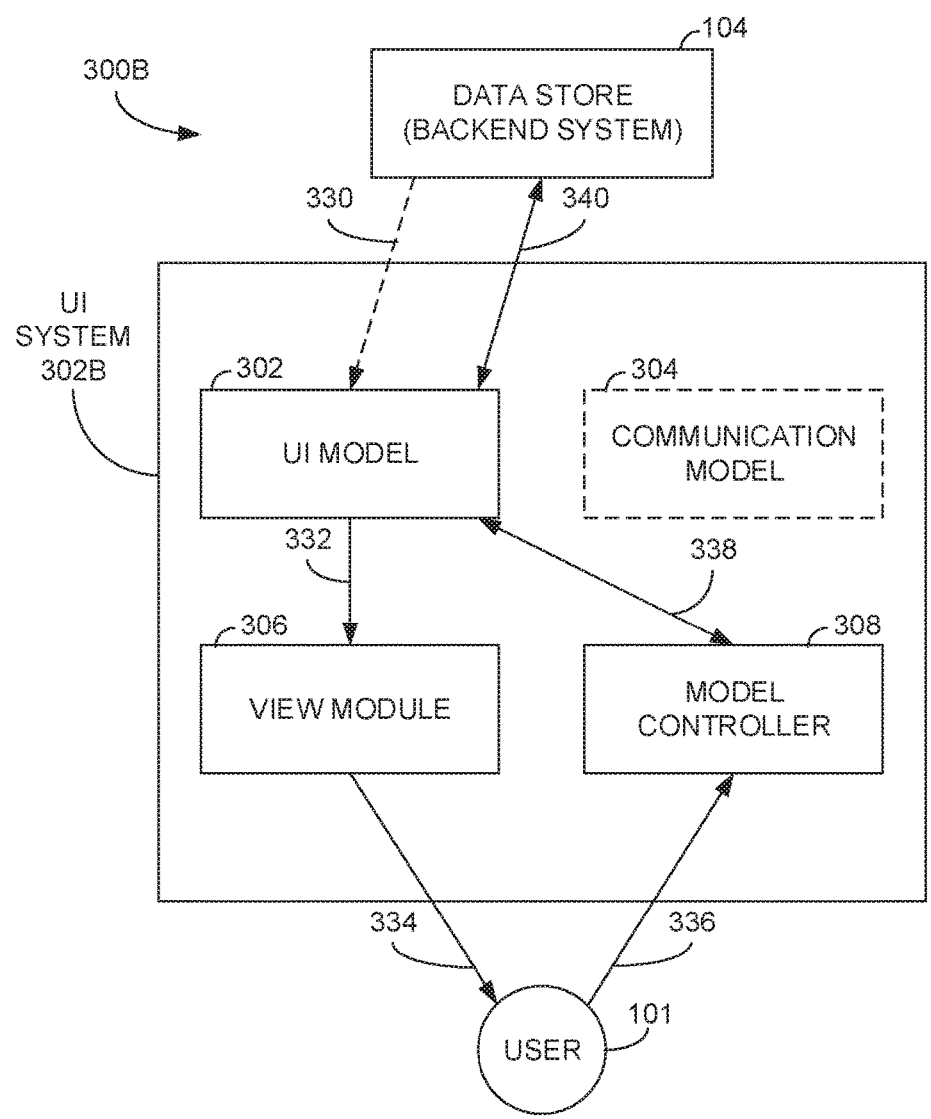
FIG. 3B is a block diagram of an example data processing system including an example user interface system employing one user interface model during a runtime of a user interface view.

After a design time of a user interface view, the user interface view may then be available to a user 101 during runtime to view, and possibly update, the values of the selected data items presented via the user interface view. FIG. 3B is a block diagram of an example data processing system 300B including an example user interface system 302B employing one user interface model during a runtime of a user interface view. As illustrated in FIG. 3B, the user interface system 302B may include the same components 302-308 discussed in conjunction with FIG. 3A. In another example embodiment, the components 302-308 of FIG. 3B may be different and separate from the similarly referenced components 302-308 of FIG. 3A.

In the user interface system 302B during runtime of a user interface view, the user interface model 302 may be configured to include first information identifying data items of the data store 104 that are being presented or exposed via the user interface view 302 to a user 101. As is the case in FIG. 3A, in some example embodiments, the plurality of data items may include fields (e.g., a key field or another field) of one or more database tables stored in the data store 104, such as data values and associations to other database tables. Further, the first information may be held in one or more data structures 330 that are initially transferred from the data store 104 to the user interface model 302 before or during the runtime of the user interface view. Also during runtime, the user interface model 302 may communicate with the data store 104 to receive updates to the data of the data items being presented in the user interface view, and also may present changes made to that data by the user 101, by way of indications 340 passed between the user interface model 302 and the data store 104.

As is the case in FIG. 3A, the view module 30 of the user interface system 302B may be configured to receive update information 332 from the user interface model 302 regarding changes or updates to the first information to be presented to the user 101. The view module 306 may also translate that information into viewable information 334 having a format utilized by the user interface system 302B, and may cause presentation of the viewable information 334 to the user 101 via the user interface system 302B.

The model controller 308 of FIG. 3B may be configured to receive user input 336 provided by the user 101 (e.g., via the user interface system 302B) and, based on that user input 336, update the user interface model 302. In an example embodiment, the user 101 may select one of the data items being presented in the user interface view, as provided by the user interface model 302 and presented by the view module 306, to request information (e.g., a value) related to that data item. In response, the model controller 308 may provide an indication 338 of that selection to the user interface model 304, which may then communicate with the data store 104 to receive the requested value via an indication 340, which may then be presented to the user 101 via the first user interface view by way of the user interface model 302 and the view module 306, communicating via update information 332, as described above.

In an example embodiment, the communication model 304 discussed above in connection with FIG. 3A may not be present in the particular user interface system 302B of FIG. 3B. In another example embodiment, the communication model 304 may be present, but not utilized, in the user interface system 302B.

Figure 4A:
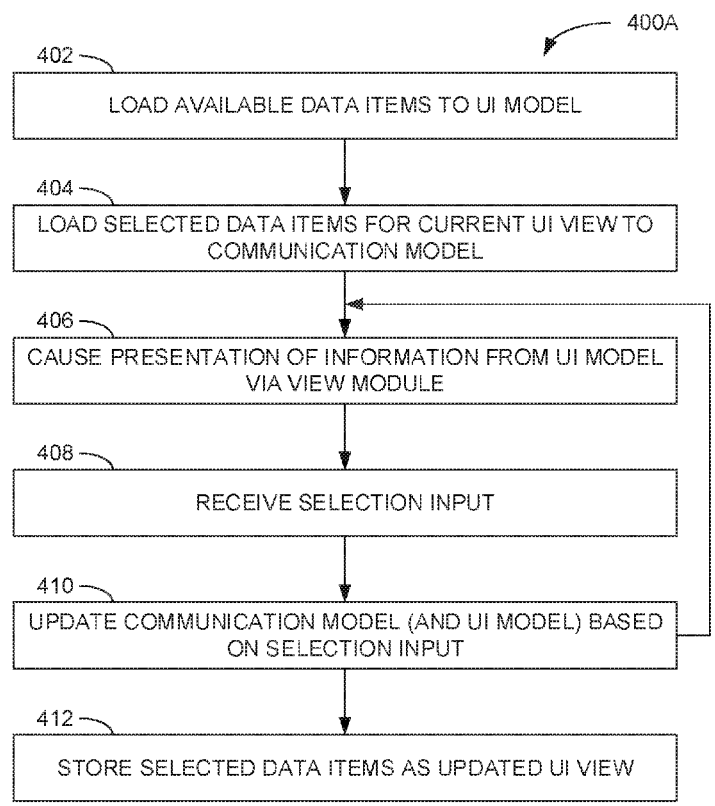
FIG. 4A is a flow diagram of an example method of operating the example user interface system of FIG. 3A.

FIG. 4A is a flow diagram of an example method 400A of operating an example user interface system (e.g., the user interface system 300A of FIG. 3A), such as during a design time of a user interface view. In the method 400A, information 310 identifying data items available from the data store 104 for use in the user interface view may be loaded from the data store 104 to the user interface model 302 (operation 402). The information identifying the available data items may also include information 312 as to which of the available data items have already been selected for use in the user interface view. The information 312 identifying the data items that have already been selected for the current user interface view may also be provided from the data store 104 to the communication model 304 (operation 404). The view module 306 may then cause the data item information in the user interface model 302 to be presented to the user 101 via a user interface (operation 406), such as via update information 314 and viewable information 316. The model controller 308 may then receive user input 318 from the user 101 indicating a selected portion of the first information (operation 408), such as a selected data item (e.g., a selected field of a database table). Based on the selected portion, the model controller 308 may update the communication model 304, and possibly the user interface model 306, to reflect a change (e.g., an addition or a deletion of a data item) to the user interface view (operation 410). In the case the user interface model 306 has been updated, that update may be presented via the view module 306 (operation 406). Also, the communication model 304 may update the data store 104 to reflect the changes to the data items included in the user interface view (operation 412), such as on an ongoing basis, or at the termination of the design time of the user interface view.

Figure 4B:
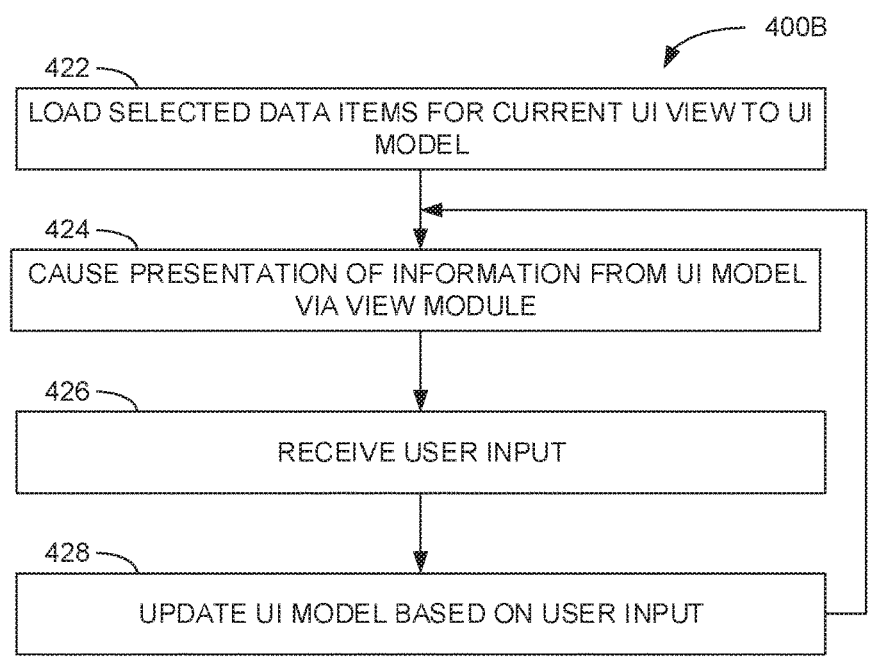
FIG. 4B is a flow diagram of an example method of operating the example user interface system of FIG. 3B.

FIG. 4B is a flow diagram of an example method 400B of operating an example user interface system (e.g., the user interface system 300B of FIG. 3B), such as during a runtime of a user interface view. In the method 400B, information 330 indicating the data items of the data store 104 associated with the current user interface view may be loaded to the user interface model 302 (operation 422). The view module 306 may cause presentation of the information in the user interface model 302 to the user 101 via a user interface (operation 424), such as by way of update information 332 and viewable information 334. The model controller 308 may receiver user input 336 provided by the user 101 in response to the information being presented to the user 101 (operation 426). In an example embodiment, the user input may be a selection of a data item to request more information related to the item. Based on the user input, the model controller 308 may update the user interface model (operation 428) by way of indication 338, such as the providing of the requested information, which may then be presented via the view module 306 to the user 101 (operation 424).

Figure 5:
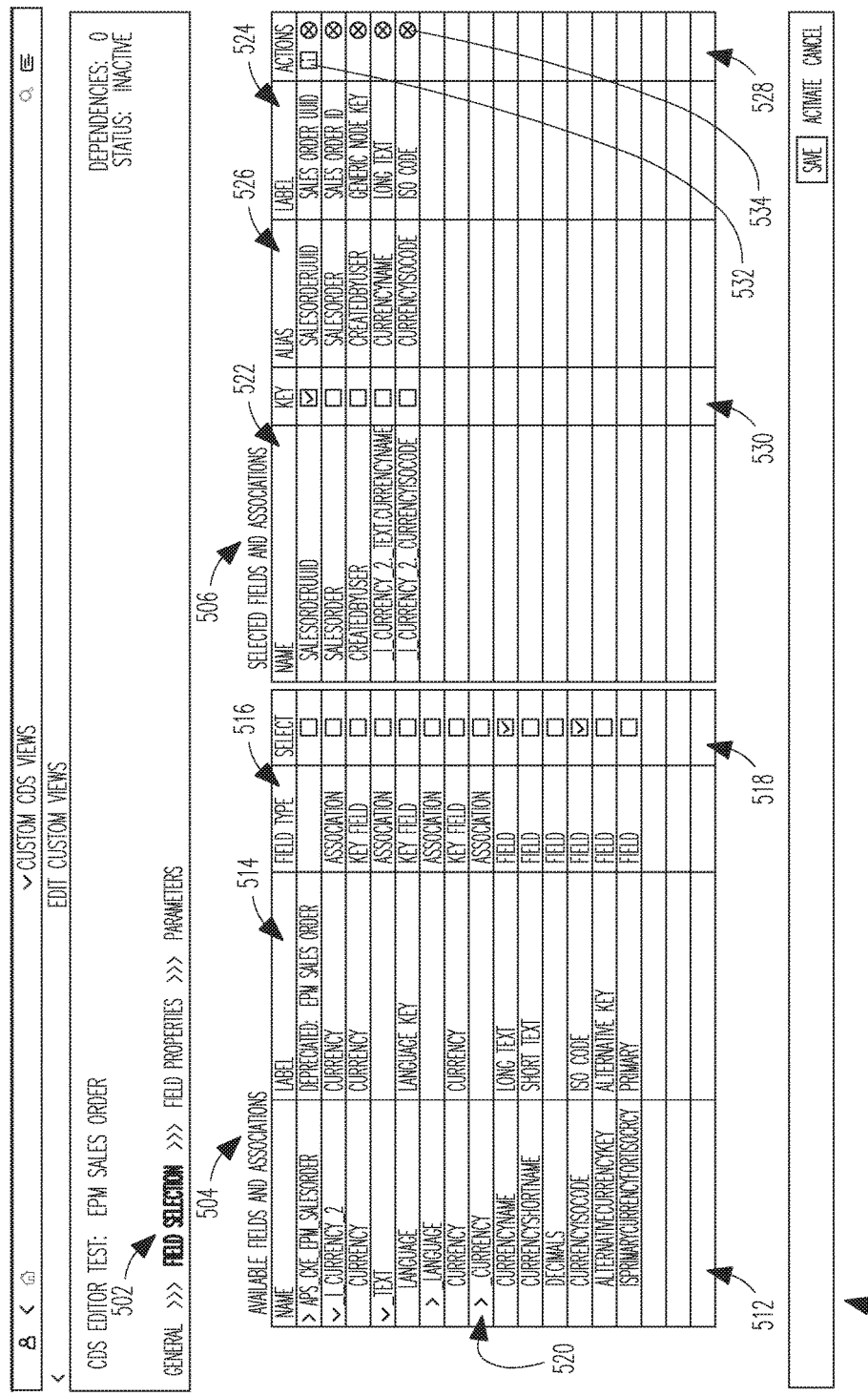
FIG. 5 is a graphical representation of an example user interface employing two user interface models during a design time of a user interface view.

FIG. 5 is a graphical representation of an example user interface employing two user interface models (e.g., the user interface model 302 and the communication model 304 of the user interface system 300A of FIG. 3A) during a design time of a user interface view. In the example embodiment of FIG. 5, the user interface 500 includes a screen 500 that facilitates user selection of available database fields for inclusion in a user interface view (e.g., a view titled "EPM Sales Order") by way of a "field selection" tab 502.

On the screen 500 are provided two displayed regions: an "available fields and associations" region 504 displaying the data items of the data store 104 that are available for inclusion in the user interface view, and a "selected fields and associations" region 506 displaying those of the available data items that the user 101 has selected for inclusion in the user interface view. In this example embodiment, the available fields and associations region 504 lists a number of fields with their associated name 512, a label 514 (if specified), and a field type 516 (e.g., a normal field, a key field, or an association with another table).

In addition, an expansion selector 520 may be displayed in conjunction with each available field of the association field type. As shown in FIG. 5, the expansion selector 520 may take the form of a simplified arrowhead whose orientation indicates whether the associated data fields being referred to by the indicated field are displayed. More specifically, a rightward-pointing arrow, as shown in conjunction with the "_Language" and "_Currency" association fields, indicates that those fields are not expanded to display the database fields of the table being associated therewith. A downward-pointing arrow, on the other hand, indicates that the fields being associated therewith are expanded and displayed. For example, the "_Text" association field has been expanded to display an associated "Language" key field, the "_Language" association field, a "Currency" key field, the "_Currency" association field, a "CurrencyName" field, and a "CurrencyShortName" field.

Also displayed with each available field of the associated fields and associations region 504 is a "select" box 518 that, when selected by the user 101, causes the corresponding field to be added to the user interface view. Conversely, a user selection of a currently filled select box 518 indicates that the corresponding field is to be removed from the resulting user interface view.

As the name suggests, the selected fields and associations region 506 displays the fields and associations from the available fields and associations region 504 that the user has selected for inclusion in the EPM Sales Order user interface view. In the particular example embodiment of FIG. 5, each selected field is presented in a list, with each selected field being displayed with its name 522, label (if applicable) 524, alias 526, key field status 530, and selectable actions 528 that may be selected by a user 101 for that particular field. For example, the selectable actions 528 area may include an "information" icon 532 which, when selected by the user 101, may provide special information particular to that field, or a "remove" icon 534 may cause the selected field to be removed from the selected fields and associations region 506.

In the particular example of screen 500, the selection of the "CurrencyISOCode" field in the available fields and associations region 504 results in that field being added as the "_I_CURRENCY_2.CurrencyISOCode" field due to the status of the "CurrencyISOCode" field as a field associated with the "_I_CURRENCY_2" field of the available fields and associations region 504. Similarly, the selection of the "CurrencyName" field in the available fields and associations region 504 results in that field being added as the "_I_CURRENCY_2._Text.CurrencyName" as a field associated with the "_Text" association of the available fields and associations region 504, which in turn is associated with the "_I_Currency_2" field of the available fields and associations region 504.

Thus, by interacting with the screen 500 as described above, a user 101 may select one or more of the fields of a data source 202, as listed in the available fields and associations region 504, to be included in the EPM Sales Order user interface view, as indicated in the selected fields and associations region 506. In an example embodiment, the user interface model 302 of FIG. 3A may include the information provided in the available fields and associations region 504 and the selected fields and associations region 506, while the communication model 304 may include the information provided in the selected fields and associations region 506.

Figure 6A:
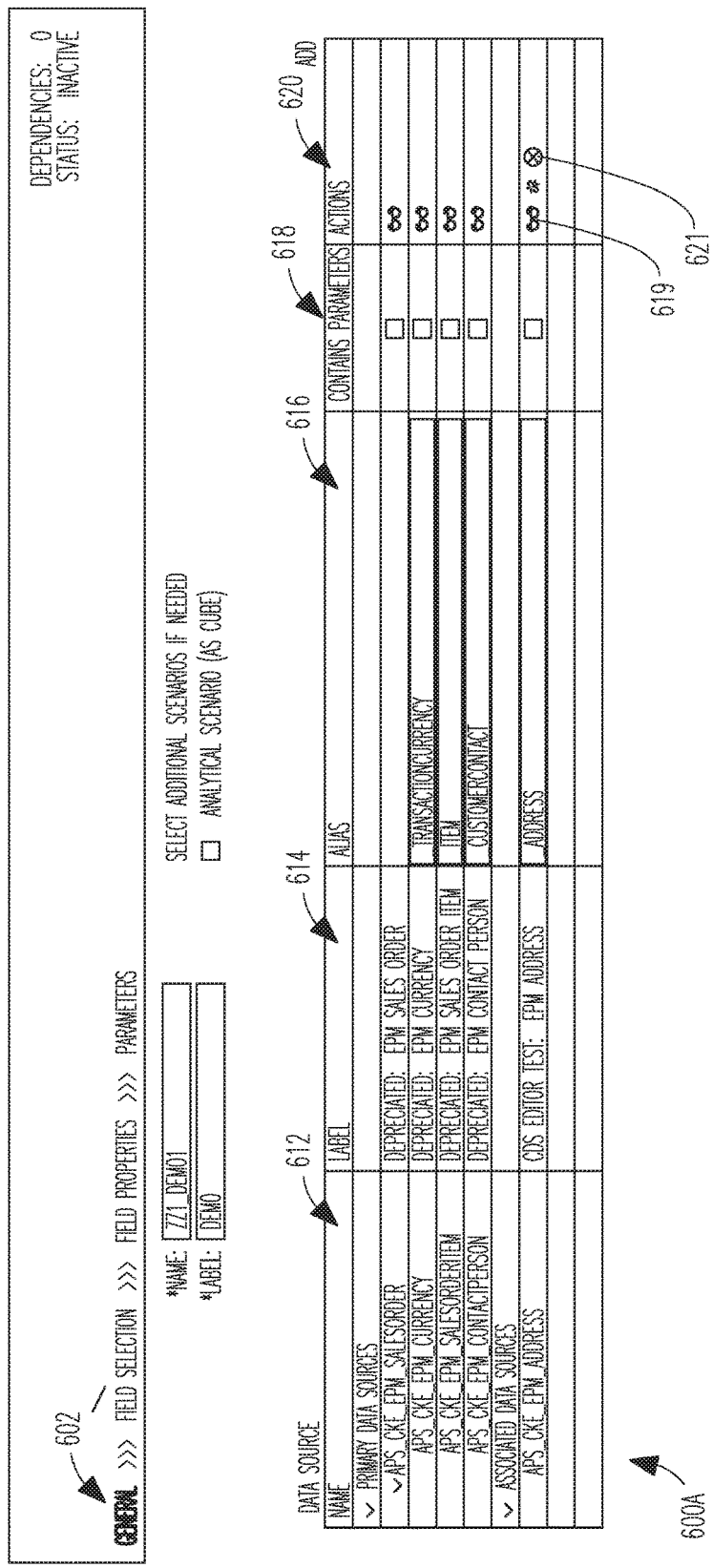
FIG. 6A is a graphical representation of an example user interface for selecting data sources for a user interface view.

As can be seen in the example of FIG. 5 discussed above, in some example embodiments, multiple levels of association between databases or database fields may be displayed to the user 101, such as in the screen 500, whereby a first association field "_I_CURRENCY_2" links to a table with a second association field "_Text", which links to both a table with a third association field "_Language" and another table with a fourth association field "_Currency". To further explain this multi-level functionality, FIGS. 6A through 6D illustrate example user interface screens provided during a design time of a user interface view. For example, FIG. 6A is a graphical representation of a screen 600A of an example user interface for selecting data sources for a user interface view. As depicted therein, the user 101 has selected a "general" tab 602 to present a list of data sources (e.g., data sources 202 of the data store 104, such as database tables) from which one or more fields may be selected for inclusion in a user interface view called "ZZ1_DEMO1". The data sources may include primary data sources, which may be provided directly by the data store 104 and may remain unmodifiable, and associated data sources (e.g., other user interface views), which may be based on primary data sources or other associated data sources, and may be modifiable. As shown in the example embodiment of FIG. 6A, displayed with each data source may be a name 612, label 614, alias 616, a parameters included indicator 618, and one or more selectable actions 620. As seen in FIG. 6A, each of the data sources may be perused in greater depth by way of a selection of an eyeglasses icon 619. Also, unlike primary data sources, associated data sources may be removed or deleted by way of a removal icon 621.

Figure 6B:
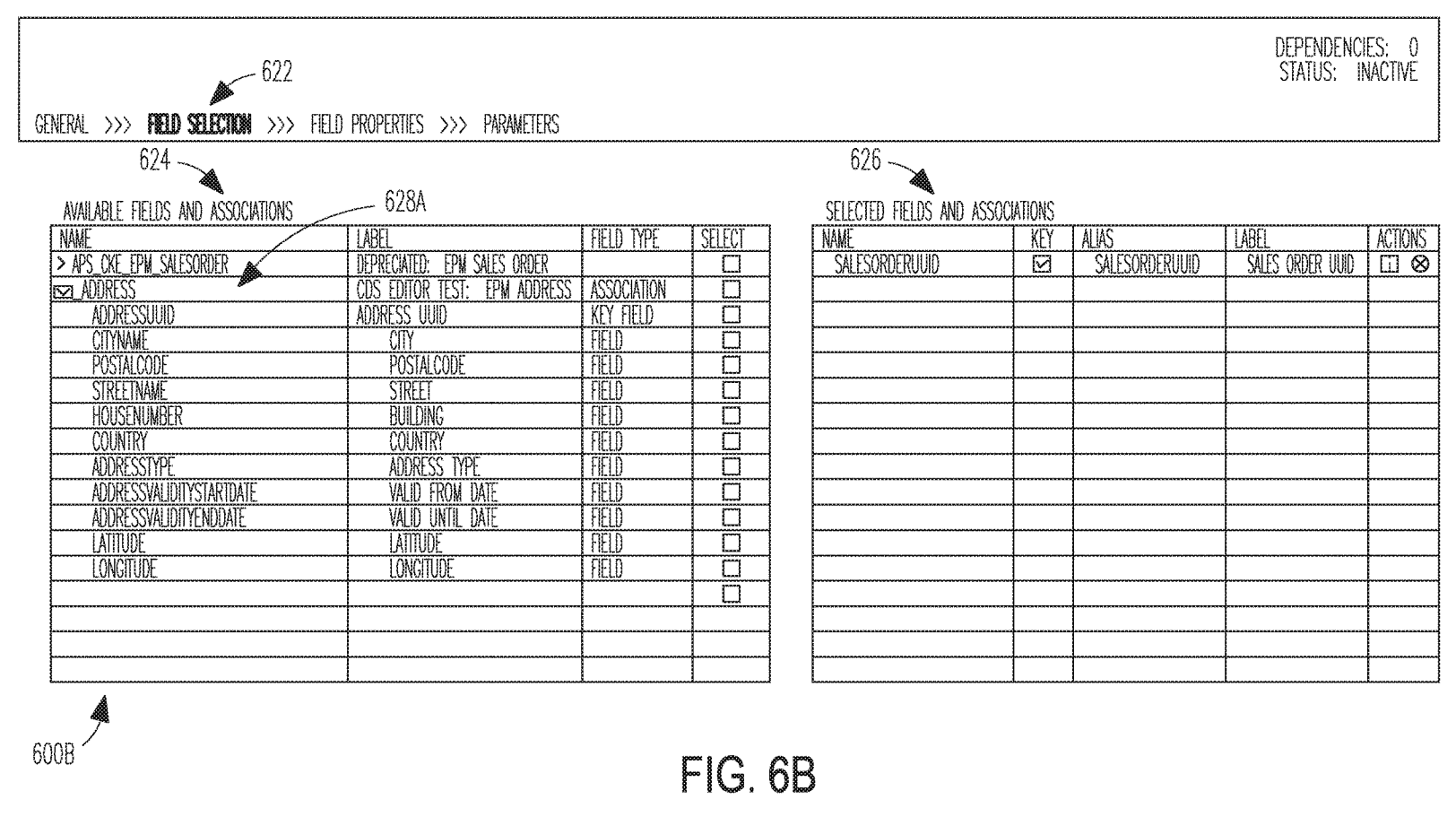

FIG. 6B is a graphical representation of a screen 600B of an example user interface for displaying selectable data items of a data source 202 for inclusion in a user interface view. The screen 600B may be presented in response to the user 101 selecting the field selection tab 622, and provide an available fields and associations region 624 and a selected fields and associations region 626 in a manner corresponding to that discussed above in conjunction with FIG. 5. As shown, an available "_ADDRESS" association field 628A of the corresponding associated data source of FIG. 6A has been expanded, as indicated by a downward-facing arrow, to display a number of fields (e.g., AddressUUID, CityName, PostalCode, and so on) of the table associated with the _ADDRESS association field. Oppositely, the "Aps_Cke_Epm_Salesorder" primary data source of FIG. 6A immediately preceding the _ADDRESS association field has not yet been expanded, as indicated by a rightward-facing arrow.

Figure 6C:
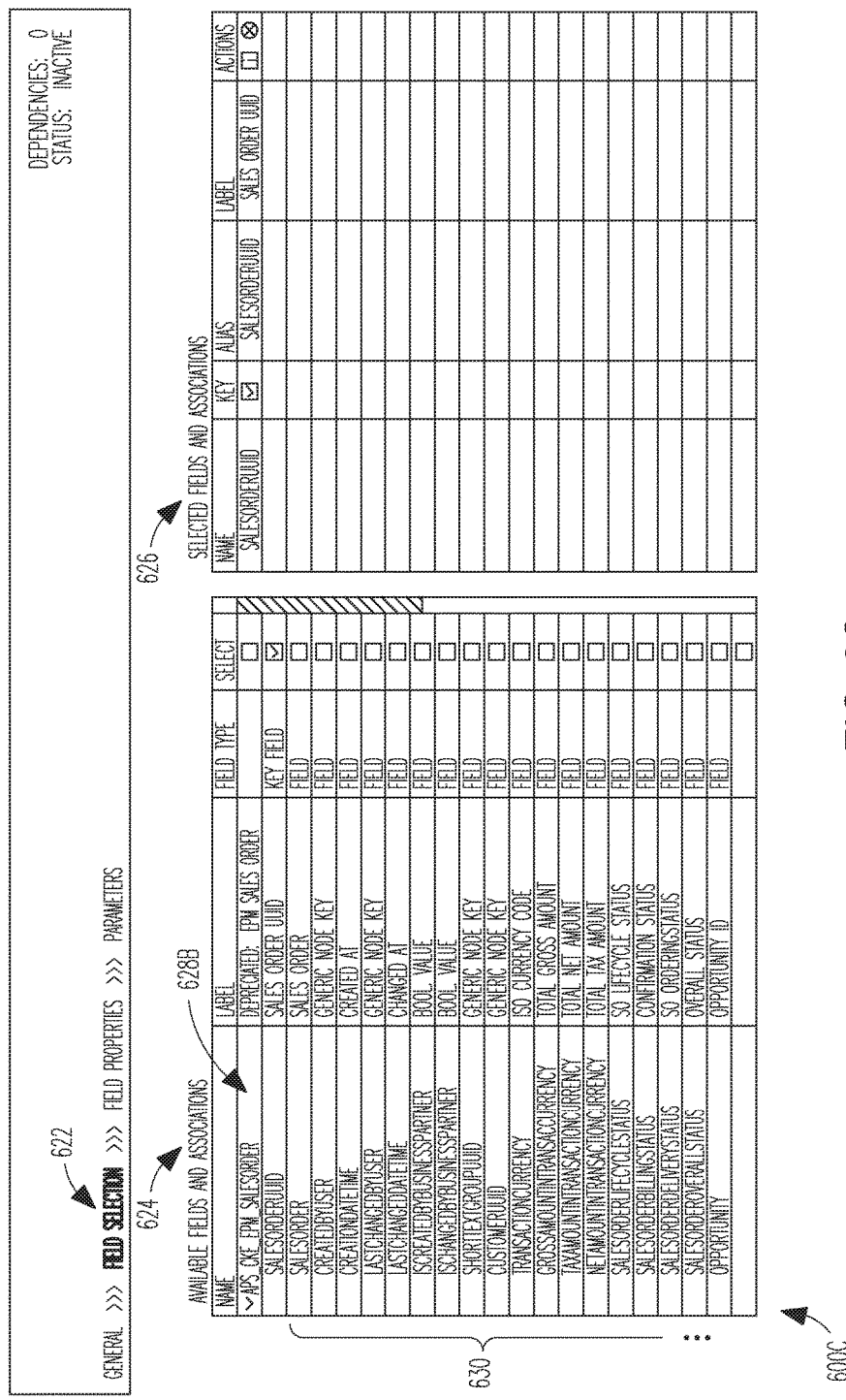

In response to the user 101 clicking the rightward-facing arrow, the Aps_Cke_Epm_Salesorder primary data source is expanded to display the fields associated with that data source 202. FIGS. 6C and 6D are graphical representations of screens 600C and 600D, respectively, of an example user interface displaying the fields in response to the expansion of the Aps_Cke_Epm_Salesorder primary data source. As shown in the screen 600C of FIG. 6C, the selected rightward-facing arrow becomes a downward-facing arrow, indicating that the Aps_Cke_Epm_Salesorder primary data source 628B is expanded to display its "SalesOrderUUID" key field and numerous other fields 630 (e.g., "SalesOrder", "CreatedByUser", "CreatedDateTime", and so forth). Also, the expansion indicates that the user has selected the SalesOrderUUID key field for inclusion in the user interface view.

In response to the user scrolling down the list of fields in the available fields and associations region 624, the screen 600D of FIG. 6D results, revealing more fields 630 of the Aps_Cke_Epm_Salesorder primary data source including a "SalesOrderPaymentTerms" field that has been selected for inclusion in the user interface view, as shown in the selected fields and associations region 626. In this example, the various fields corresponding to an expanded association field are indented to further emphasize the relationship between the two different levels of fields being displayed.

Also shown within the fields 630 of the Aps_Cke_Epm_Salesorder primary data source in screen 600D is a "_TransactionCurrency" association field that has been expanded by the user 101 to show its corresponding fields: a "Currency" key field and a "CurrencyISOCode" field, of which the Currency key field has also been selected by the user for addition to the user interface view, as listed in the selected fields and associations region 626 as the "_TransactionCurrency.Currency" field. These corresponding fields are indented relative to their corresponding association field to further emphasize the difference in association levels being displayed.

Consequently, the user interface depicted at least in FIGS. 6B through 6D provides the ability to display at least two levels of association among database tables in a single user interface screen, thus facilitating navigation by the user 101 through the various association levels for selecting particular fields during a design time of a user interface view. In example embodiments, a limit to the number of association levels that may be displayed at once (e.g., five levels) may be imposed by the user interface system 302A to limit the size of the data structures representing those levels, which may be passed between the data store 104 and the user interface model 302, for example. In other example embodiments, display may be limited to some other number of levels, or no such level limit may be imposed.

Figure 7:
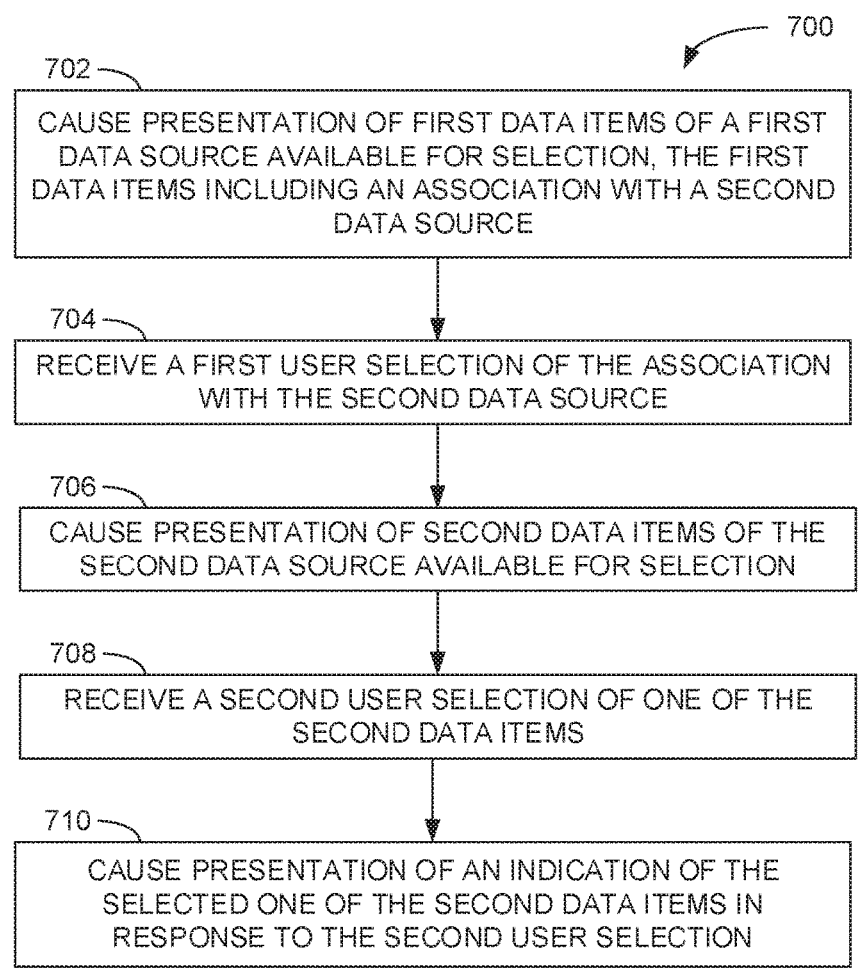
FIG. 7 is a flow diagram of an example method of presenting multiple associated levels of selectable data fields for inclusion in a user interface view.

FIG. 7 is a flow diagram of an example method 700 of presenting multiple associated levels of selectable data fields for inclusion in a user interface view. In the method 700, the view module 306 may cause presentation of first data items of a first data source (e.g., a primary data source, an associated data source, a database table, or the like) available for selection in a user interface view (operation 702) (e.g., as indicated in the user interface view 302), with the first data items including an association with a second data source. The model controller 308 may then receive a first user selection of the association with the second data source (operation 704), and may update the user interface model 302 accordingly. The view module 306 may then cause presentation of second data items of the second data source that are available for selection (operation 706) (e.g., as indicated in the updated user interface view 302). The model controller 306 may then receive a second user interface selection of one of the second data items (operation 708), and may update the user interface model 302 again. Based on the updated user interface model 302, the view module 306 may cause presentation of an indication of the selected one of the second data items (operation 710). In an example embodiment, the second user selection may be of an association with a third data source, resulting in third data items of the third data source to be displayed. In another example embodiment, the second user selection may be a field selected for inclusion in the user interface view.

The information regarding the data sources and their multiple levels of association may be stored in any number of different types of data structures, such as a nested array. FIG. 8 is a listing of an example data object 800 that describes a data source, and is structured as a nested array that includes multiple associated levels of selectable data fields for possible inclusion in a user interface view. In this example embodiment, the data object 800 includes four different sections: a root identifier 802 indicating a possible root object to which the data object 800 refers, a field list 804 (e.g., a one-dimensional array) of twenty-seven fields, an association list of three in length 820, and a parameter list 822 of length zero. The last field 806 of the field list 804 is expanded to reveal the data of its corresponding association field, having a name 808 of "_CustomerContact" and a field type 810 of "A" (e.g., designating an association field), along with a label, a "noChangeAllowed" flag to indicate whether the field 806 may be changed, and a change type for the field 806.

Also in included in the field 806 of the field list 804, as shown in FIG. 8, is an annotation, data type information, association information, and another field list 812 (e.g., another one-dimensional array within an element of the first one-dimensional array) of eighteen fields to which the association field 806 refers. The eighteenth field 814 is displayed in expanded form to reveal its name 815 ("_Address"), a field type 816 (e.g., an association field), and other information, including yet another nested field list 818 or one-dimensional array. In various example embodiments, the fields of the nested array of the object 800 may be stored in a single extent of memory in a serial format, as distributed blocks of memory linked with pointers, or according to another data structure format.

In an example embodiment, the nested array may be constructed using descriptions of the various database tables and their fields that are available for selection in a user interface view. In one example embodiment, the user interface model 302 may access these descriptions and parse them to build the nested array or other data structure to provide the multi-level presentation.

Figure 9:
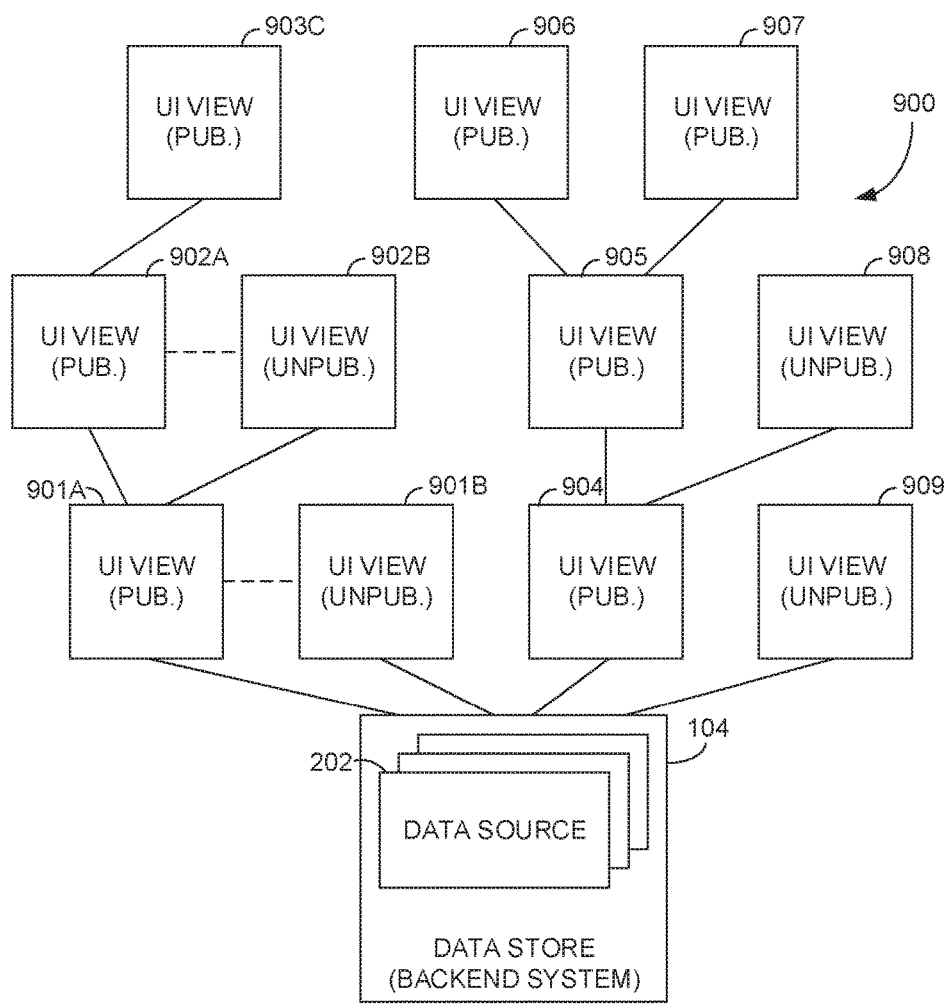
FIG. 9 is a block diagram describing example relationships between various levels of published and unpublished user interface views.

FIG. 9 is a block diagram of a data view hierarchy 900 describing example relationships between various levels of published (e.g., active) and unpublished (e.g., inactive) user interface views. In this specific example embodiment, several user interface views 901A, 902B, 904, and 909 are based directly on one or more data sources 202 of the data store 104, which may be database tables or other user interface views. More specifically, user interface view 901A is a published user interface view, indicating that other user interface views may be based directly or indirectly upon that view 901A. An unpublished version 901B of the published interface view 901A, on the other hand, is not available as a data source for other user interface views. The separate published user interface view 904 has no corresponding unpublished version, while the unpublished user interface view 909 has no corresponding published version.

Continuing with FIG. 9, a published user interface view 902A and a corresponding unpublished version 902B both refer directly to the published user interface view 901A, while another published user interface view 903C is based directly on the published user interface view 902A. Also, two separate published user interface views 906, 907 depend upon a published user interface view 905 that, in turn, is based on the published user interface view 904, while an unpublished user interface view 908 not related to the published user interface view 905 also depends directly from the published user interface view 904. In some example embodiments, a user interface view, whether published or unpublished, may depend from more than one other user interface view.

Given the dependencies between various published and unpublished user interface views, with some published and unpublished views being related versions of each other, the various possible dependencies between the views that enable simple customization of user interface views by basing some views on other similar views may also cause potential problems when a view that serves as a basis for another view is modified. For example, the deletion of a data item (e.g., a database field) from one view may cause the malfunction of another higher-level view that depends upon the modified view, such as if the deleted data item is also being employed in the higher-level view.

Figure 10:
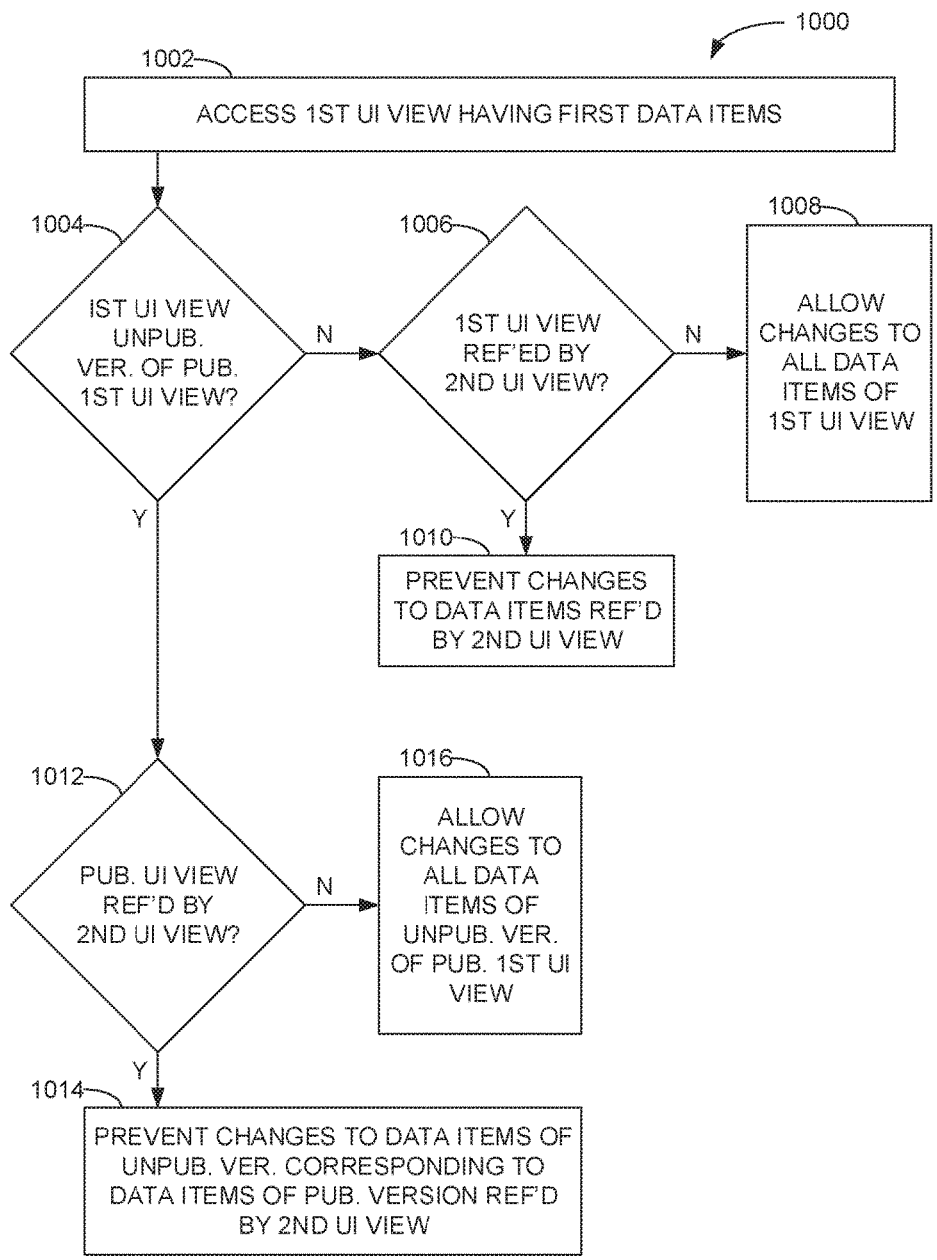
FIG. 10 is a flow diagram of an example method of enforcing compatibility rules in changes to user interface views.

To prevent a user 101 from making changes to one view that are incompatible with another view, some example embodiments of the user interface system 300A may employ a compatibility rule-checking function to prevent user interface view changes that are incompatible with other dependent views. FIG. 10 is a flow diagram of an example method 1000 of enforcing compatibility rules in changes to user interface views. In an example embodiment, the user interface model 302 may perform the various operations of FIG. 10. However, one or more other portions of the user interface system 300A may perform these operations in other example embodiments.

In the method 1000, a first user interface view having first data items is accessed (operation 1002). In an example embodiment, the data store 104 provides the first user interface view as one or more data structures to the user interface model 302, as discussed above. If the first user interface view is an unpublished version of a published user interface view (operation 1004), and the published user interface view is referenced by a second user interface view (operation 1012) (e.g., the second user interface view incorporates data items used in the published user interface view), than changes are prevented to data items of the unpublished version of the first user interface view corresponding to data items of the published version of the first user interface view that are referenced by the second user interface view (operation 1014). If, instead, the first user interface view is an unpublished version of a published user interface view (operation 1004), but the published user interface view is not referenced by a second user interface view (operation 1012), then changes are allowed to all of the data items of the unpublished version of the first user interface view (operation 1016).

If, instead, the first user interface view is not an unpublished version of a published first user interface view (operation 1004) (e.g., the first user interface view is an unpublished version of the first user interface view without a corresponding published version, or the first user interface view is a published version), but the first user interface view is referenced by a second user interface view (operation 1006) (e.g., a second user interface view incorporates data items used in a published first user interface view), then changes are prevented to data items of the first user interface view that are referenced by the second user interface view (operation 1010). Otherwise, if the first user interface view is not an unpublished version of a published first user interface view (operation 1004), and the first user interface view is not referenced by a second user interface view (operation 1006) (e.g., a second user interface view does not incorporate data items used in a published first user interface view, or the first user interface view is unpublished), then changes are allowed to all data items of the first user interface view (operation 1008).

Figure 11:
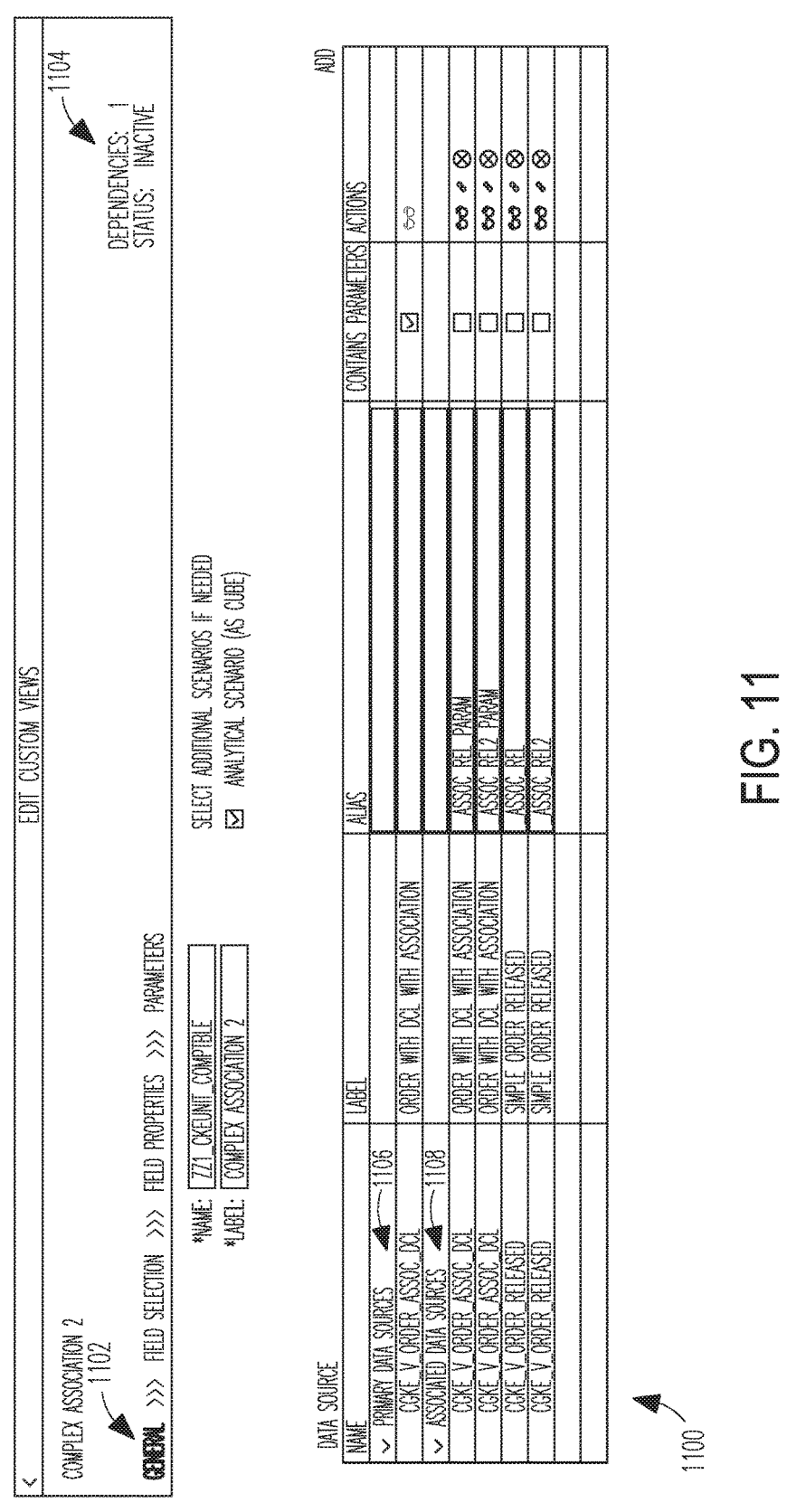

In conjunction with FIG. 10, FIG. 11 is a graphical representation of a screen 1100 of an example user interface for selecting data sources for a user interface view in which data dependency data and user interface view status are provided. In the screen 1100, which may be presented to a user 101 as a result of the user 101 selecting a "general" tab 1102 during a design time of a user interface view, a number of primary data sources 1106 (e.g., data sources that may be provided directly by the data store 104 and may remain unmodifiable) and associated data sources 1108 (e.g., data sources that may be based on primary data sources or other associated data sources, and may be modifiable) are presented via a user interface. Also shown in the screen 1100 is a dependency and status indicator 1104 showing a number of user interface views that refer to any published versions of current user interface view (one, in this example) and a version status of the interface view ("inactive", or unpublished, in this case).

Figure 12:
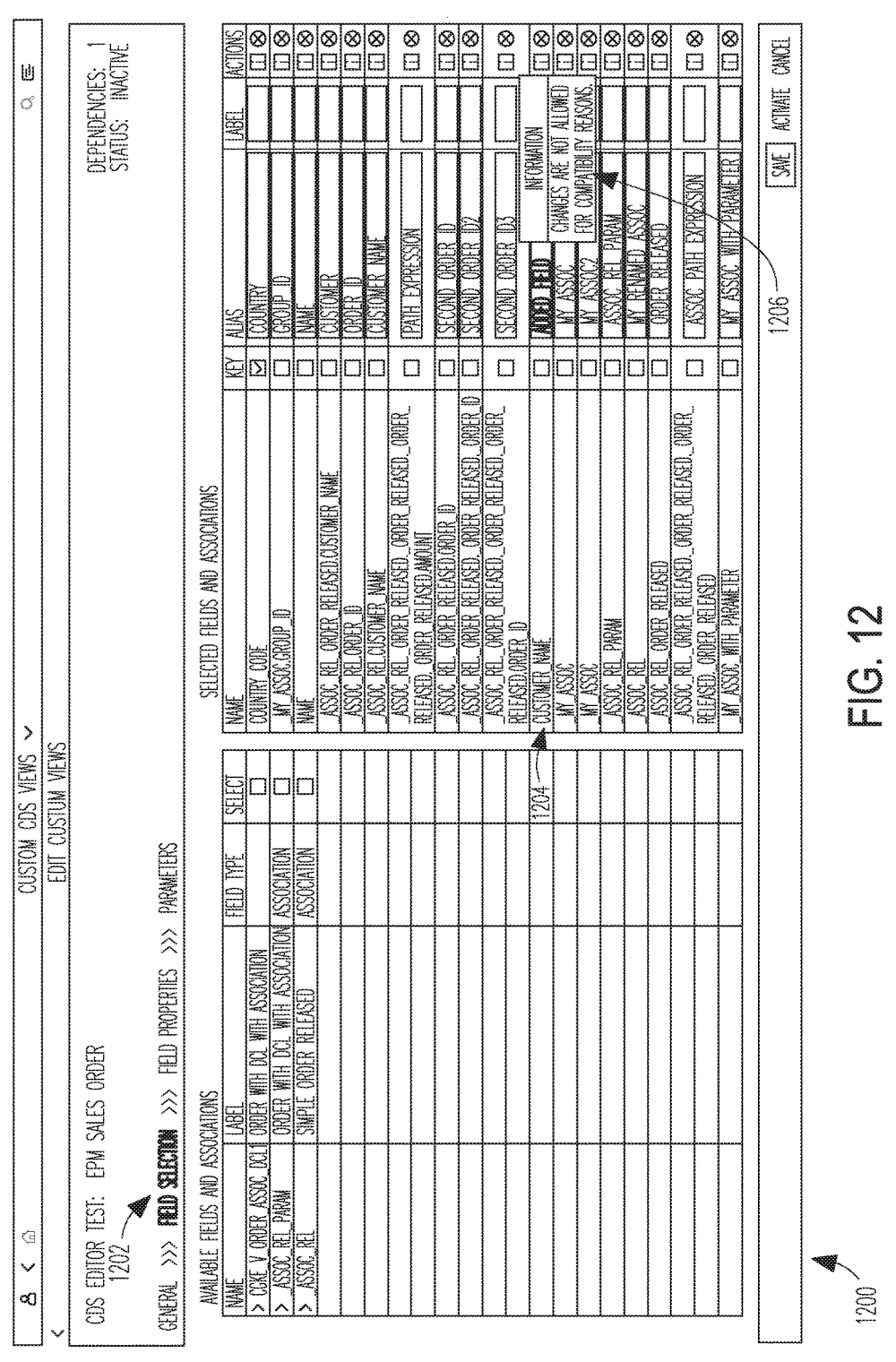

FIG. 12 is a graphical representation of a screen 1200 of an example user interface for displaying selectable data items of a data source for inclusion in a user interface view in which change compatibility guidance is provided and/or incompatible changes are prevented. In this example embodiment, the screen 1200 is presented to the user 101 in response to the user 101 selecting a "field selection" tab 1202 on the user interface. In the particular example of FIG. 12, primary data source "COKE_V_ORDER_ASSOC_DCL1" and associated data sources "_assoc_ref_param" and "_assoc_ref" (indicated as association fields in screen 1200 of FIG. 12) are presented as available fields and associations based on the information provided in the screen 1100 of FIG. 11. Among the fields selected by the user 101 for inclusion in the unpublished version of the user interface view (as shown in the "selected fields and associations" list) are several fields (e.g., "country_code", "_my_assoc.group_is", "name", and so on) of the published version of the user interface view, and one field ("CUSTOMER_NAME") that was previously added only to the unpublished version from one of the data sources 202, and thus is not included in the published version of the user interface view.

In response to this particular user interface view structure, the screen 1200 may be configured to prevent the user 101 from making changes (e.g., name changes, annotation changes, field deletions, etc.) to the multiple data items employed in the published version of the user interface view. Additionally, the screen 1200 may visually indicate the inability of the user 101 to make such alterations, such as by, for example, graying out the alias and label fields of the data items to which changes are prevented. Also, the screen 1200 may provide information icons that, when clicked or otherwise selected, may provide information 1206 that indicates changes are not possible (e.g., "Changes are not allowed for compatibility reasons."). Oppositely, the single field that was added to the unpublished version over the published version of the user interface view includes a user-modifiable alias and does not provide a cautionary message or icon that would indicate an inability to be renamed, deleted, or otherwise altered.

Consequently, in the example embodiments of FIGS. 9 through 12, changes to various versions of user interface views may be allowed or prevented based on various data dependencies among the various versions. In some example embodiments, changes to a published version of a user interface view upon which other user interface views depend (either directly or indirectly via other user interface views) may be allowed only for those data items that are not included in the dependent views. Further, changes to an unpublished version of a user interface view that corresponds to a published version may be limited to those fields that either are not included in the published version, or are included in the published version but are not referenced by another user interface view, to prevent incompatibility conflicts if and when the unpublished version is chosen as the published version of the view.

In an example embodiment, a system comprises one or more hardware processors and a memory storing instructions that, when executed by at least one of the one or more hardware processors, cause the system to perform operations comprising accessing a first user interface view comprising a first plurality of data items, each of the first plurality of data items referencing a corresponding data item of a data source; determining whether the first user interface view is referenced by a second user interface view; based on the first user interface view not being referenced by a second user interface view, allowing changes to any of the first plurality of data items of the first user interface view during a design time of the first user interface view; based on the first user interface view being referenced by a second user interface view, identifying one or more of the first plurality of data items of the first user interface view being referenced by the second user interface view; and preventing changes to at least the one or more of the first plurality of data items of the first user interface view during the design time of the first user interface view.

In another example embodiment, including all previous example embodiments, the determining whether the first user interface view is referenced by a second user interface view comprises determining whether the first user interface view is directly referenced by a second user interface view or indirectly referenced by a second user interface view through another user interface view.

In another example embodiment, including all previous example embodiments, the changes allowed comprise at least one of a deletion of one or more of the first plurality of data items of the first user interface view, a renaming of one or more of the first plurality of data items of the first user interface view, or changing an annotation of one or more of the first plurality of data items of the first user interface view.

In another example embodiment, including all previous example embodiments, the one or more of the first plurality of data items comprise at least one of a database field or a database association.

In another example embodiment, including all previous example embodiments, the operations further comprise allowing changes to others of the first plurality of data items of the first user interface view not identified as being referenced by the second user interface view during the design time of the first user interface view.

In another example embodiment, including all previous example embodiments, the identifying one or more of the first plurality of data items of the first user interface view being referenced by the second user interface view comprises identifying one or more of the first plurality of data items of the first user interface view being referenced directly by the second user interface view or indirectly by the second interface view via another user interface view.

In another example embodiment, including all previous example embodiments, the preventing of changes to the one or more of the first plurality of data items of the first user interface view comprises preventing at least one of a deletion or a renaming of the one or more of the first plurality of data items of the first user interface view.

In another example embodiment, including all previous example embodiments, the operations further comprise causing, on a user interface, presentation of at least some of the first plurality of data items of the first user interface view; and indicating, on the user interface, those of the one or more of the first plurality of data items of the first user interface view to which changes are prevented.

In another example embodiment, including all previous example embodiments, the indicating of those of the one or more of the first plurality of data items of the first user interface view to which changes are prevented comprises causing, on the user interface, presentation of an icon indicating the preventing of changes for each of those of the one or more of the first plurality of data items of the first user interface view to which changes are prevented.

In another example embodiment, including all previous example embodiments, the operations further comprise based on the first user interface view comprising a published version of the first user interface view corresponding to an unpublished version of the first user interface view, and based on one or more of the first plurality of data items of the published version of the first user interface view being referenced by the second user interface, preventing changes to one or more of the first plurality of data items of the unpublished version of the first user interface view corresponding to the one or more of the first plurality of data items of the first user interface view during the design time of the unpublished version of the first user interface view, and allowing changes to others of the first plurality of data items of the unpublished version of the first user interface view not corresponding to the one or more of the first plurality of data items of the first user interface view during the design time of the unpublished version of the first user interface view.

In another example embodiment, including all previous example embodiments, the first user interface view is one of a published version of the first user interface view or an unpublished version of the first user interface view without a corresponding published version of the first user interface view.

In another example embodiment, including all previous example embodiments, the operations further comprise determining a number of second user interface views that reference the first user interface view; and causing, via a user interface, presentation of the number of second user interface views that reference the first user interface view.

In an example embodiment, a method comprises accessing a first user interface view comprising a first plurality of data items, each of the first plurality of data items referencing a corresponding data item of a data source; determining whether the first user interface view is referenced by a second user interface view; based on the first user interface view not being referenced by a second user interface view, using one or more hardware processors of a machine, allowing changes to any of the first plurality of data items of the first user interface view during a design time of the first user interface view; based on the first user interface view being referenced by a second user interface view, identifying one or more of the first plurality of data items of the first user interface view being referenced by the second user interface view; and preventing changes to the one or more of the first plurality of data items of the first user interface view during the design time of the first user interface view.

In another example embodiment, including all previous example embodiments, allowing changes to others of the first plurality of data items of the first user interface view not identified as being referenced by the second user interface view during the design time of the first user interface view.

In another example embodiment, including all previous example embodiments, the identifying one or more of the first plurality of data items of the first user interface view being referenced by the second user interface view comprises identifying one or more of the first plurality of data items of the first user interface view being referenced directly by the second user interface view or indirectly by the second interface view via another user interface view.

In another example embodiment, including all previous example embodiments, the operations further comprise causing, on a user interface, presentation of at least some of the first plurality of data items of the first user interface view; and indicating, on the user interface, those of the one or more of the first plurality of data items of the first user interface view to which changes are prevented.

In another example embodiment, including all previous example embodiments, the indicating of those of the one or more of the first plurality of data items of the first user interface view to which changes are prevented comprises causing, on the user interface, presentation of an icon indicating the preventing of changes for each of those of the one or more of the first plurality of data items of the first user interface view to which changes are prevented.

In another example embodiment, including all previous example embodiments, the operations further comprise based on the first user interface view comprising a published version of the first user interface view corresponding to an unpublished version of the first user interface view, and based on one or more of the first plurality of data items of the published version of the first user interface view being referenced by the second user interface, preventing changes to one or more of the first plurality of data items of the unpublished version of the first user interface view corresponding to the one or more of the first plurality of data items of the first user interface view during the design time of the unpublished version of the first user interface view, and allowing changes to others of the first plurality of data items of the unpublished version of the first user interface view not corresponding to the one or more of the first plurality of data items of the first user interface view during the design time of the unpublished version of the first user interface view.

In another example embodiment, including all previous example embodiments, the first user interface view is one of a published version of the first user interface view or an unpublished version of the first user interface view without a corresponding published version of the first user interface view.

In an example embodiment, a non-transitory computer-readable storage medium storing instructions that, when executed by one or more hardware processors of a machine, cause the machine to perform operations comprising accessing a first user interface view comprising a first plurality of data items, each of the first plurality of data items referencing a corresponding data item of a data source; determining whether the first user interface view is referenced by a second user interface view; based on the first user interface view not being referenced by a second user interface view, allowing changes to any of the first plurality of data items of the first user interface view during a design time of the first user interface view; based on the first user interface view being referenced by a second user interface view, identifying one or more of the first plurality of data items of the first user interface view being referenced by the second user interface view; and preventing changes to the one or more of the first plurality of data items of the first user interface view during the design time of the first user interface view.

Figure 13:
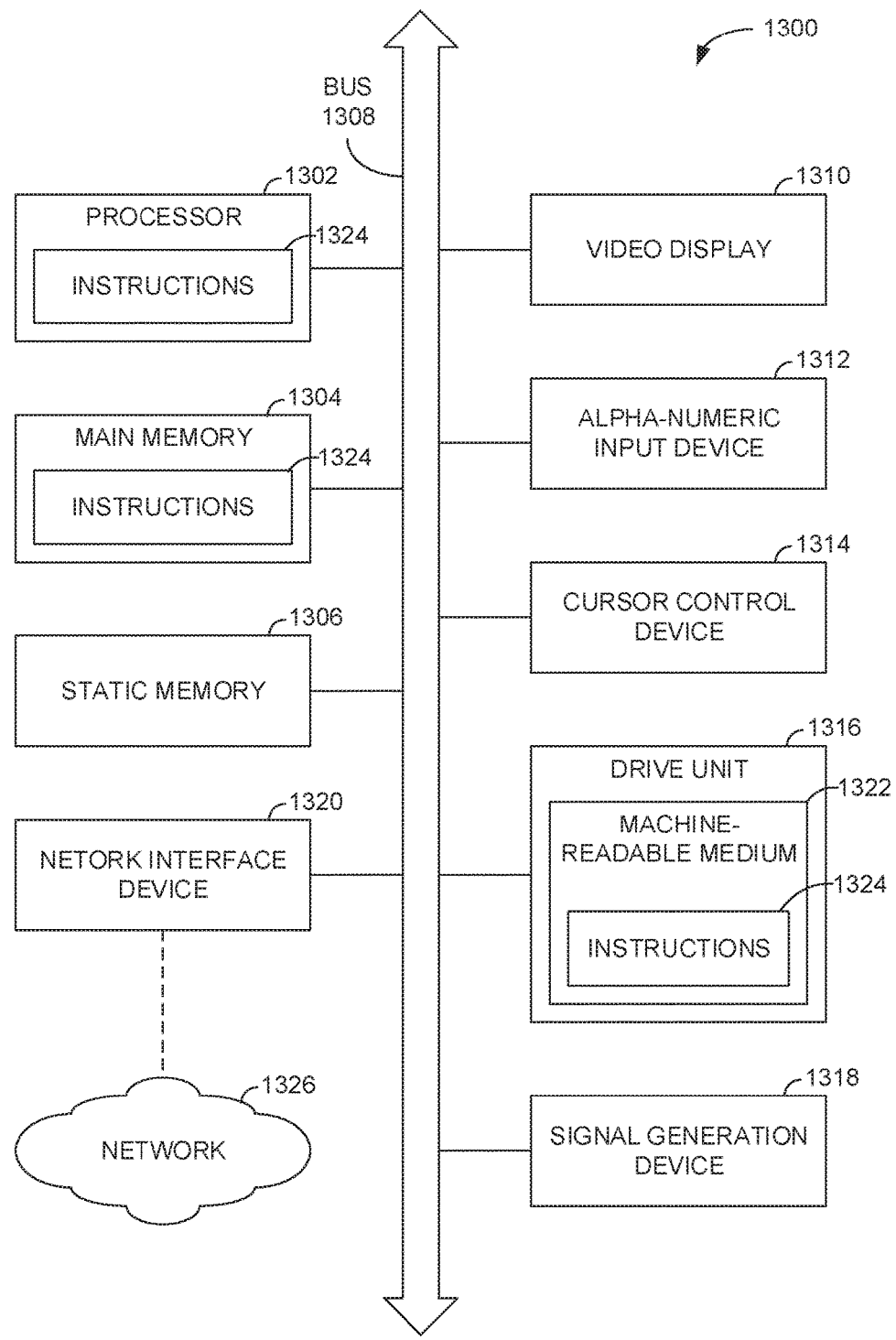
FIG. 13 is a block diagram of a computer processing system within which a set of instructions may be executed for causing a computer to perform any one or more of the methodologies discussed herein.

FIG. 13 is a block diagram of a computer processing system 1300 within which a set of instructions 1324 may be executed for causing a computer to perform any one or more of the methodologies discussed herein, such as those discussed in conjunction with FIGS. 4A, 4B, 7, and 10, as well as other methodologies discussed herein. In some embodiments, the computer operates as a standalone device or may be connected (e.g., networked) to other computers. In a networked deployment, the computer may operate in the capacity of a server or a client computer in server-client network environment, or as a peer computer in a peer-to-peer (or distributed) network environment. Moreover, the computer processing system 1300 may serve in example embodiments as, for example, the user interface system 102, 302A, and 302B described above, as well as any component, model, or module described therewith.

In addition to being sold or licensed via traditional channels, embodiments may also be deployed, for example, by software-as-a-service (SaaS), application service provider (ASP), or by utility computing providers. The computer may be a server computer, a personal computer (PC), a tablet PC, a personal digital assistant (PDA), a cellular telephone, or any processing device capable of executing a set of instructions (sequential or otherwise) that specify actions to be taken by that device. Further, while only a single computer is illustrated, the term "computer" shall also be taken to include any collection of computers that, individually or jointly, execute a set (or multiple sets) of instructions to perform any one or more of the methodologies discussed herein.

The example computer processing system 1300 includes a processor 1302 (e.g., a central processing unit (CPU), a graphics processing unit (GPU), or both), a main memory 1304, and a static memory 1306, which communicate with each other via a bus 1308. The computer processing system 1300 may further include a video display 1310 (e.g., a plasma display, a liquid crystal display (LCD), or a cathode ray tube (CRT)). The computer processing system 1300 also includes an alphanumeric input device 1312 (e.g., a keyboard), a user interface (UI) cursor control device 1314 (e.g., a mouse and/or touch screen), a drive unit 1316, a signal generation device 1318 (e.g., a speaker), and a network interface device 1320.

The drive unit 1316 includes a machine-readable medium 1322 on which is stored one or more sets of instructions 1324 and data structures embodying or utilized by any one or more of the methodologies or functions described herein. The instructions 1324 may also reside, completely or at least partially, within the main memory 1304, the static memory 1306, and/or within the processor 1302 during execution thereof by the computer processing system 1300, the main memory 1304, the static memory 1306, and the processor 1302 also constituting tangible machine-readable media 1322.

The instructions 1324 may further be transmitted or received over a network 1326 via the network interface device 1320 utilizing any one of a number of well-known transfer protocols (e.g., Hypertext Transfer Protocol).

While the machine-readable medium 1322 is shown in an example embodiment to be a single medium, the term "machine-readable medium" should be taken to include a single medium or multiple media (e.g., a centralized or distributed database, and/or associated caches and servers) that store the one or more sets of instructions 1324. The term "machine-readable medium" shall also be taken to include any medium that is capable of storing, encoding, or carrying a set of instructions 1324 for execution by the computer and that cause the computer to perform any one or more of the methodologies of the present application, or that is capable of storing, encoding, or carrying data structures utilized by or associated with such a set of instructions 1324. The term "machine-readable medium" shall accordingly be taken to include, but not be limited to, solid-state memories and optical and magnetic media.

While the example embodiments discussed herein are described with reference to various implementations and exploitations, these example embodiments are illustrative, and the scope of the disclosure is not so limited. In general, techniques for maintaining consistency between data structures may be implemented with facilities consistent with any hardware system or hardware systems defined herein. Many variations, modifications, additions, and improvements are possible.

Plural instances may be provided for components, operations, or structures described herein as a single instance. Finally, boundaries between various components, operations, and data stores are somewhat arbitrary, and particular operations are illustrated in the context of specific illustrative configurations. Other allocations of functionality are possible and may fall within a scope of various embodiments of the present disclosure. In general, structures and functionality presented as separate components in the exemplary configurations may be implemented as a combined structure or component. Similarly, structures and functionality presented as a single component may be implemented as separate components. These and other variations, modifications, additions, and improvements fall within a scope of embodiments of the present disclosure as represented by the appended claims.

What is claimed is:

1. A system comprising:
    one or more hardware processors; and
    a memory storing instructions that, when executed by at least one of the one or more hardware processors, cause the system to perform operations comprising:
        accessing a first user interface view comprising a first plurality of data items, each of the first plurality of data items referencing a corresponding data item of a data source;
        determining whether the first user interface view is referenced by a second user interface view;
        based on the first user interface view not being referenced by a second user interface view, allowing changes to any of the first plurality of data items of the first user interface view during a design time of the first user interface view;
        based on the first user interface view being referenced by a second user interface view, identifying one or more of the first plurality of data items of the first user interface view being referenced by the second user interface view; and
        preventing changes to at least the one or more of the first plurality of data items of the first user interface view during the design time of the first user interface view.

2. The system of claim 1, the determining whether the first user interface view is referenced by a second user interface view comprising determining whether the first user interface view is directly referenced by a second user interface view or indirectly referenced by a second user interface view through another user interface view.

3. The system of claim 1, the changes allowed comprising at least one of a deletion of one or more of the first plurality of data items of the first user interface view, a renaming of one or more of the first plurality of data items of the first user interface view, or changing an annotation of one or more of the first plurality of data items of the first user interface view.

4. The system of claim 3, the one or more of the first plurality of data items comprising at least one of a database field or a database association.

5. The system of claim 1, the operations further comprising:
    allowing changes to others of the first plurality of data items of the first user interface view not identified as being referenced by the second user interface view during the design time of the first user interface view.

6. The system of claim 5, the identifying one or more of the first plurality of data items of the first user interface view being referenced by the second user interface view comprising identifying one or more of the first plurality of data items of the first user interface view being referenced directly by the second user interface view or indirectly by the second interface view via another user interface view.

7. The system of claim 5, the preventing of changes to the one or more of the first plurality of data items of the first user interface view comprising preventing at least one of a deletion or a renaming of the one or more of the first plurality of data items of the first user interface view.

8. The system of claim 5, the operations further comprising
    causing, on a user interface, presentation of at least some of the first plurality of data items of the first user interface view; and
    indicating, on the user interface, those of the one or more of the first plurality of data items of the first user interface view to which changes are prevented.

9. The system of claim 8, the indicating of those of the one or more of the first plurality of data items of the first user interface view to which changes are prevented comprising causing, on the user interface, presentation of an icon indicating the preventing of changes for each of those of the one or more of the first plurality of data items of the first user interface view to which changes are prevented.

10. The system of claim 5, the operations further comprising:
based on the first user interface view comprising a published version of the first user interface view corresponding to an unpublished version of the first user interface view, and based on one or more of the first plurality of data items of the published version of the first user interface view being referenced by the second user interface, preventing changes to one or more of the first plurality of data items of the unpublished version of the first user interface view corresponding to the one or more of the first plurality of data items of the first user interface view during the design time of the unpublished version of the first user interface view, and allowing changes to others of the first plurality of data items of the unpublished version of the first user interface view not corresponding to the one or more of the first plurality of data items of the first user interface view during the design time of the unpublished version of the first user interface view.

11. The system of claim 1, the first user interface view being one of a published version of the first user interface view or an unpublished version of the first user interface view without a corresponding published version of the first user interface view.

12. The system of claim 1, the operations further comprising:
determining a number of second user interface views that reference the first user interface view; and
causing, via a user interface, presentation of the number of second user interface views that reference the first user interface view.

13. A method comprising:
accessing a first user interface view comprising a first plurality of data items, each of the first plurality of data items referencing a corresponding data item of a data source;
determining whether the first user interface view is referenced by a second user interface view;
based on the first user interface view not being referenced by a second user interface view, using one or more hardware processors of a machine, allowing changes to any of the first plurality of data items of the first user interface view during a design time of the first user interface view;
based on the first user interface view being referenced by a second user interface view, identifying one or more of the first plurality of data items of the first user interface view being referenced by the second user interface view; and
preventing changes to the one or more of the first plurality of data items of the first user interface view during the design time of the first user interface view.

14. The method of claim 13, further comprising:
allowing changes to others of the first plurality of data items of the first user interface view not identified as being referenced by the second user interface view during the design time of the first user interface view.

15. The method of claim 14, the identifying one or more of the first plurality of data items of the first user interface view being referenced by the second user interface view comprising identifying one or more of the first plurality of data items of the first user interface view being referenced directly by the second user interface view or indirectly by the second interface view via another user interface view.

16. The method of claim 14, the operations further comprising:
causing, on a user interface, presentation of at least some of the first plurality of data items of the first user interface view; and
indicating, on the user interface, those of the one or more of the first plurality of data items of the first user interface view to which changes are prevented.

17. The method of claim 16, the indicating of those of the one or more of the first plurality of data items of the first user interface view to which changes are prevented comprising causing, on the user interface, presentation of an icon indicating the preventing of changes for each of those of the one or more of the first plurality of data items of the first user interface view to which changes are prevented.

18. The method of claim 14, the operations further comprising:
based on the first user interface view comprising a published version of the first user interface view corresponding to an unpublished version of the first user interface view, and based on one or more of the first plurality of data items of the published version of the first user interface view being referenced by the second user interface, preventing changes to one or more of the first plurality of data items of the unpublished version of the first user interface view corresponding to the one or more of the first plurality of data items of the first user interface view during the design time of the unpublished version of the first user interface view, and allowing changes to others of the first plurality of data items of the unpublished version of the first user interface view not corresponding to the one or more of the first plurality of data items of the first user interface view during the design time of the unpublished version of the first user interface view.

19. The method of claim 13, the first user interface view being one of a published version of the first user interface view or an unpublished version of the first user interface view without a corresponding published version of the first user interface view.

20. A non-transitory computer-readable storage medium storing instructions that, when executed by one or more hardware processors of a machine, cause the machine to perform operations comprising:
accessing a first user interface view comprising a first plurality of data items, each of the first plurality of data items referencing a corresponding data item of a data source;
determining whether the first user interface view is referenced by a second user interface view;
based on the first user interface view not being referenced by a second user interface view, allowing changes to any of the first plurality of data items of the first user interface view during a design time of the first user interface view;
based on the first user interface view being referenced by a second user interface view, identifying one or more of the first plurality of data items of the first user interface view being referenced by the second user interface view; and
preventing changes to the one or more of the first plurality of data items of the first user interface view during the design time of the first user interface view.

* * * * *